(12) United States Patent
Walsh et al.

(10) Patent No.: US 11,850,149 B2
(45) Date of Patent: Dec. 26, 2023

(54) PROSTHETIC HEART VALVE DELIVERY SYSTEM

(71) Applicants: Brandon Walsh, Kaysville, UT (US); Matthew F. Ogle, Edina, MN (US)

(72) Inventors: Brandon Walsh, Kaysville, UT (US); Matthew F. Ogle, Edina, MN (US)

(*) Notice: Subject to any disclaimer, the term of this patent is extended or adjusted under 35 U.S.C. 154(b) by 331 days.

(21) Appl. No.: 17/192,531

(22) Filed: Mar. 4, 2021

(65) Prior Publication Data
US 2021/0275300 A1 Sep. 9, 2021

Related U.S. Application Data

(60) Provisional application No. 62/985,653, filed on Mar. 5, 2020.

(51) Int. Cl.
*A61F 2/962* (2013.01)
*A61F 2/95* (2013.01)
*A61F 2/24* (2006.01)

(52) U.S. Cl.
CPC .......... *A61F 2/2418* (2013.01); *A61F 2/2439* (2013.01); *A61F 2/9517* (2020.05); *A61F 2220/0016* (2013.01); *A61F 2220/0083* (2013.01)

(58) Field of Classification Search
CPC .... A61F 2/2418; A61F 2/2436; A61F 2/2439; A61F 2/243; A61F 2/2433; A61F 2/82; A61F 2/9517; A61F 2/966; A61F 2002/9665; A61F 2/24; A61F 2/962; A61F 2/95
See application file for complete search history.

(56) References Cited

U.S. PATENT DOCUMENTS

| | | | | |
|---|---|---|---|---|
| 4,957,479 A | * | 9/1990 | Roemer | A61F 2/95 604/8 |
| 9,192,500 B1 | * | 11/2015 | Longo | A61F 2/06 |
| 9,387,101 B2 | * | 7/2016 | Dorn | A61F 2/97 |
| 9,877,858 B2 | * | 1/2018 | Beard | A61F 2/97 |
| 9,931,232 B2 | * | 4/2018 | Gunderson | A61F 2/95 |
| 10,835,258 B1 | * | 11/2020 | Pillai | A61B 17/12109 |
| 11,020,255 B2 | * | 6/2021 | Rincon | A61F 2/95 |
| 11,413,175 B2 | * | 8/2022 | McHugo | A61F 2/962 |
| 11,426,173 B2 | * | 8/2022 | Pillai | A61B 17/12031 |
| 11,439,492 B2 | * | 9/2022 | Walzman | A61B 8/06 |
| 2001/0004696 A1 | * | 6/2001 | Roberts | A61F 2/95 606/108 |
| 2005/0177182 A1 | * | 8/2005 | van der Burg | A61B 17/12022 606/157 |
| 2006/0282155 A1 | * | 12/2006 | Fearn | A61M 39/0613 623/1.12 |
| 2007/0067012 A1 | * | 3/2007 | George | A61F 2/915 623/1.12 |

(Continued)

*Primary Examiner* — Seema Mathew
(74) *Attorney, Agent, or Firm* — Steven Rinehart

(57) ABSTRACT

A prosthetic heart valve and delivery system adapted to facilitate transapical or transfemoral implantation of a prosthetic heart valve, the delivery system comprising an elongated sheath or shaft have one or more loop stabilization wires adapted to circumscribe and crimp a metallic stent, the loop stabilization wires releasable with retraction of an engagement pin to expand the metallic stent and anchor the same in native tissue within the circulatory system of a patient.

12 Claims, 18 Drawing Sheets

(56) References Cited

U.S. PATENT DOCUMENTS

| | | | | |
|---|---|---|---|---|
| 2007/0293930 A1* | 12/2007 | Wang | .................... | A61F 2/95 |
| | | | | 623/1.11 |
| 2008/0255651 A1* | 10/2008 | Dwork | .................... | A61F 2/95 |
| | | | | 623/1.11 |
| 2009/0099640 A1* | 4/2009 | Weng | .................... | A61F 2/95 |
| | | | | 623/1.11 |
| 2010/0100055 A1* | 4/2010 | Mustapha | ......... | A61M 25/0075 |
| | | | | 604/525 |
| 2011/0307049 A1* | 12/2011 | Kao | .................... | A61F 2/966 |
| | | | | 623/1.11 |
| 2013/0289697 A1* | 10/2013 | Baker | ............... | A61M 25/0053 |
| | | | | 156/244.11 |
| 2015/0305902 A1* | 10/2015 | Argentine | ............... | A61F 2/966 |
| | | | | 623/1.12 |
| 2016/0074188 A1* | 3/2016 | Ryan | ................... | A61F 2/962 |
| | | | | 623/1.12 |
| 2017/0056222 A1* | 3/2017 | Bradway | ............... | A61F 2/9517 |
| 2018/0000620 A1* | 1/2018 | Folan | ................... | A61F 2/966 |
| 2018/0014932 A1* | 1/2018 | Hammer | ............... | A61F 2/2418 |
| 2018/0116843 A1* | 5/2018 | Schreck | ................ | A61F 2/2418 |
| 2019/0076279 A1* | 3/2019 | Halbert | ................ | A61F 2/966 |
| 2020/0107838 A1* | 4/2020 | Pillai | ................ | A61B 17/12031 |
| 2020/0214716 A1* | 7/2020 | Pillai | ................ | A61F 2/013 |
| 2020/0297491 A1* | 9/2020 | Argento | ................ | A61F 2/2457 |
| 2022/0265446 A1* | 8/2022 | Taniguchi | ................ | A61F 2/90 |
| 2022/0313461 A1* | 10/2022 | Hasegawa | ............... | A61F 2/844 |
| 2022/0409860 A1* | 12/2022 | Castelli | ............ | A61M 25/0147 |
| 2023/0088094 A1* | 3/2023 | Bradway | ............... | A61F 2/9517 |
| | | | | 606/108 |
| 2023/0140867 A1* | 5/2023 | Sakurada | ................ | A61F 2/966 |
| | | | | 623/23.7 |

* cited by examiner

PROSTHETIC HEART VALVE DELIVERY SYSTEM

BACKGROUND OF THE INVENTION

Field of the Invention

The present invention relates generally to the field of prosthetic heart valves and more specifically relates to a delivery system for prosthetic heart valves and a method of transcatheter delivery of a valve through the cardiovascular system.

Description of the Related Art

The human heart is the muscular organ which pumps blood through the circulatory system. The natural heart valves are identified as the aortic, mitral (or bicuspid), tricuspid and pulmonary valves. The four chambers of the heart are identified as the upper left, the right atria, the lower left, and right ventricle. This combination of chambers and valves allows only one-way blood flow during the complete pumping cycle of the heart.

Prosthetic heart valves are used to replace damaged or diseased heart valves, commonly in the aortic and mitral valves. These heart valves can be damages or x underdeveloped by congenital, inflammatory, or infectious conditions, or simple old age. Typically, a surgeon accesses the heart through the thoracic cavity via a sternotomy. The patient is placed on cardiopulmonary bypass, thereafter, allowing access to the heart and the replacement of heart valves.

The percutaneous delivery of heart valves as an alternative to conventional valve replacement is known in the art and referred to as percutaneous aortic valve replacement (PAVR) or percutaneous aortic valve implantation (PAVI). Transcatheter valves can be provided via a transfemoral (via the upper leg), subclavian (beneath the collar bone), transvenous, or transcardia routes. The valve prothesis may be attached to calcified leaflets of heart valves within the valve annuli. Accessing native valves in this manner typically allows for reduced trauma, less hospital stay and improved patient recovery, over alternatives method of delivery such as sternotomy.

Patients and surgeons attempting PAVI face a number of challenges, including stenosed (contracted or narrowed) blood vessels too small in diameter to accommodate through passage of traditional delivery systems and prosthetic heart valves, often caused by plaque, previous surgeries, or tortuosity of path. Additionally, aortic valve are typically delivered using a balloon-expandable delivery system in which crimped prosthetic heart valves (or compressed stents) are advanced through blood vessels to the target site and mounted in place within the annulus using an inflatable balloon adapted to expand the prosthetic heart valve to its functional size.

Careful deployment of the valve prosthesis is critical to allow secure attachment and anatomical alignment, allowing optimal valve performance. Native valves with stenosis (i.e., calcification) can provide a surface that aids in attachment of the valve prostheses. In aortic regurgitation, leaflets may not have the amount of calcification needed for secure engagement of the valve prosthesis.

Because of the difficult in placing a stent, many stents are misplaced. There exists no efficient means in the art of slightly adjusting a stent about to be deployed at the delivery site. For this reason, new stents must periodically replace, or be implanted within, older stents. These older stents may lack the surface morphology necessary for new valve implantation. There is a need in the art for a prothesis which may be placed into prosthetic valves previously put in place.

The valves and delivery systems known in the art lack features which overcome these difficulties presented by challenging anatomical conditions.

These balloon delivery systems suffer from a number of drawbacks, including insufficient expansive force of the balloon to properly place the prothesis, and insufficient resistance once placed with the leaflets. The annulus in which the prothesis is placed may expand over time and result in displacement of the prothesis and migration away from the ventricle.

Systems and methods which address controlled deployment and attachment of the prosthesis is critical to optimal prosthetic valve performance. Accordingly, it is desirable to devise additional systems to allow transcatheter delivery of a valve prosthesis.

The foregoing examples of the related art and limitations related therewith are intended to be illustrative and not exclusive. Other limitations of the related art will become apparent to those of skill in the art upon a reading of the specification and a study of the drawings.

SUMMARY

From the foregoing discussion, it should be apparent that a need exists for an improved prosthetic heart valve and delivery system. The present invention has been developed in response to the present state of the art, and in particular, in response to the problems and needs in the art that have not yet been fully solved by currently available inventions. Accordingly, the present invention has been developed to provide a prosthetic heart valve and delivery system comprising: a spring-biased, metallic stent adapted to radially expand and contract comprising: a plurality of crisscrossing laths forming a cylindrical body, and a flexible check valve formed from one or more compressible valvular elements mounted within an interior recess formed by the crisscrossing laths; a plurality of declined stabilization prongs protruding laterally from one or more laths in the expanded metallic stent configuration; a selectively steerable delivery system comprising: a handle comprising a plurality of controls adapted to apply tensile force to one or more pull wires, the handle defining a hollow through passageway, an elongated sheath affixed at a proximal end to the handle, the elongated sheath comprising a flexible tubular member; wherein the one or more pull wires longitudinally traverse a lumen within the delivery system; one or more stabilization wire(s) forming annular rings at a distal end of the sheath, the annular rings adapted to receive, circumscribe and crimp the metallic stent, the stabilization wires protruding from one or more apertures on the distal end, the stabilization loops forming one or more subloops within one of the sheath and a lumen; an engagement pin detachably inserted into the subloop(s) of the stabilization wire(s), the engagement pin connected with a pull wire to a control on the handle, the engagement pin adapted to retract proximally out of the subloop(s) when the control is activated, the engagement pin adapted to release the annular rings and allow the metallic stent to expand; a frustoconical tip; wherein the sheath defines an annular recess at a distal end behind the frustoconical tip, the annular recess adapted to receive the metallic stent in compressed configuration.

The lumen may be the elongated sheath.

The elongated sheath may be between 60 and 150 cm long on a longitudinal axis. The one or more loop stabilization wire(s) may be positioned within the annular recess. The metallic stent may be detachably circumscribed by the loop stabilization wires.

The prosthetic heart valve and delivery system may further comprise a tapered hub at the distal end behind the frustoconical tip. The frustoconical tip may define a hollow nose cone passageway traversing the frustoconical tip longitudinally.

The one or more loop stabilization wire(s) may form subloops within the annular recess. The compressed metallic stent may be between 3 mm and 10 mm in diameter and the expanded metallic stent is between 10 mm and 40 mm in diameter.

A second prosthetic heart valve and delivery system is provided comprising: a spring-biased, metallic stent adapted to radially expand and contract comprising: a plurality of crisscrossing laths, and a flexible check valve formed from one or more compressible valvular elements mounted within an interior recess formed by the crisscrossing laths; a plurality of stabilization prongs protruding laterally from one or more laths in the expanded metallic stent configuration; a selectively steerable delivery system comprising: a handle comprising a plurality of controls adapted to apply tensile force to one or more pull wires, the handle defining a hollow through passageway, an elongated sheath affixed at a proximal end to the handle, the elongated sheath comprising a flexible tubular member; wherein the one or more pull wires longitudinally traverse a lumen within the delivery system; one or more stabilization wire(s) forming annular rings at a distal end of the sheath, the annular rings adapted to receive, circumscribe and crimp the metallic stent, the stabilization wires protruding from one or more apertures on the distal end, the stabilization loops forming one or more subloops within one of the sheath and a lumen; an engagement pin detachably inserted into the subloop(s) of the stabilization wire(s), the engagement pin connected with a pull wire to a control on the handle, the engagement pin adapted to retract proximally out of the subloop(s) when the control is activated, the engagement pin adapted to release the annular rings and allow the metallic stent to expand; a tapered tip; a tapered hub forming a second annular recess through which a rigid stabilization loop protrudes; a rigid stabilization loop adapted to telescope relative to the frustoconical tip, the rigid stabilization loop declining laterally and toward the distal end, the rigid stabilization loop adapted to engage soft tissue and adjust positioning of the delivery system within a patient's circulatory system; wherein the sheath defines an annular recess at a distal end behind the frustoconical tip, the annular recess adapted to receive the metallic stent in compressed configuration; wherein the one or more loop stabilization wire(s) form subloops within the annular recess.

The elongated sheath may be between 60 and 150 cm long on a longitudinal axis. The metallic stent, in some embodiments, may be detachably circumscribed by the loop stabilization wires.

In various embodiments, the prosthetic heart valve and delivery system further comprises a tapered hub at the distal end behind the frustoconical tip. The frustoconical tip may define a hollow nose cone passageway traversing the frustoconical tip longitudinally.

A third prosthetic heart valve and delivery system is provided comprising: a spring-biased, metallic stent; a selectively steerable delivery system comprising: a handle comprising a plurality of controls adapted to apply tensile force to one or more pull wires, the handle defining a hollow through passageway, an elongated sheath affixed at a proximal end to the handle, the elongated sheath comprising a flexible tubular member; wherein the one or more pull wires longitudinally traverse one or more of a lumen and the sheath; one or more stabilization wire(s) forming annular rings at a distal end of the sheath, the annular rings adapted to receive, circumscribe and crimp the metallic stent, the stabilization wires protruding from one or more apertures on the distal end, the stabilization wires adapted to expand at a delivery point in a patient's vascular system and deploy the metallic stent; a frustoconical tip; wherein the sheath defines an annular recess at a distal end behind the frustoconical tip, the annular recess adapted to receive the metallic stent in compressed configuration.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
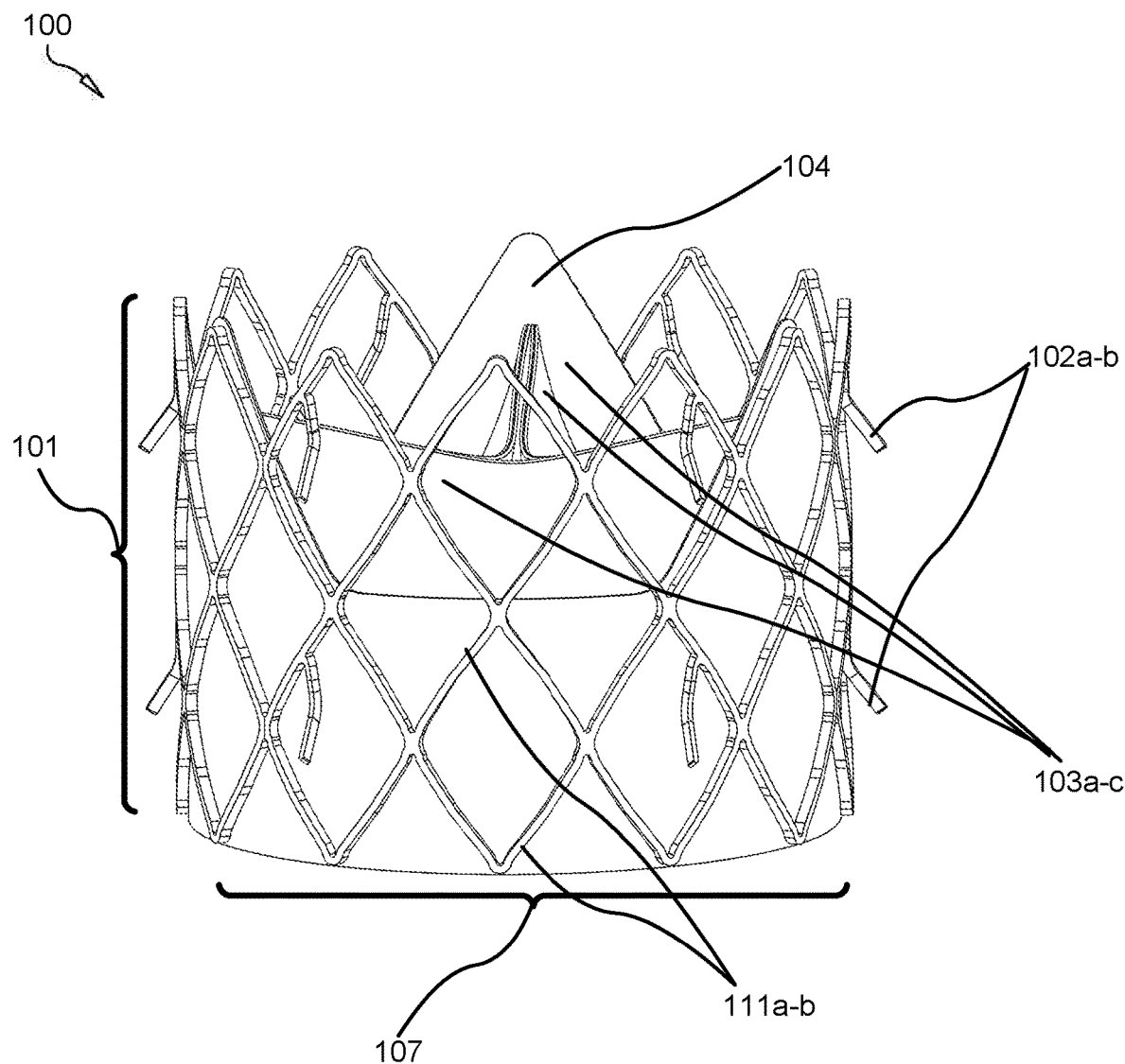
FIG. 1 illustrates a forward perspective view of an aortic valve prosthesis assembly with self-expanding frame in accordance with the present invention.

Reference throughout this specification to "one embodiment," "an embodiment," or similar language means that a particular feature, structure, or characteristic described in connection with the embodiment is included in at least one embodiment of the present invention. Appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are provided. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Objects of the Present Invention

It is an object of the present invention to provide an apparatus, system, and method for valve replacement, preferably using a minimally invasive surgical technique. While the systems and methods will have application in a number of different vessels in various parts of the body, they are particularly well suited for replacement of a malfunctioning cardiac valve, and in particular an aortic valve. The systems and methods will also have application in other malfunctioning cardiac valves, e.g., a pulmonary valve or a mitral valve. The systems and methods are particularly advantageous in their ability to provide a more flexible prosthetic heart valve delivery system, ensure accurate and precise placement of the prosthetic heart valve or valve prosthesis with reduced reliance on imaging, and provide additional attachment of the valve prosthesis, reducing the incidence of valve migration. Another advantage is the delivery and implantation of the valve prosthesis through the aorta, which has a smaller diameter than the inferior vena cava, through which surgeons typically proceed to access the heart.

It is further an object of the present invention to provide improved systems and methods for implanting a prosthetic heart valve. In particular, improved minimally invasive methods and systems are provided for retrograde implantation of expansible prosthetic heart valves within or adjacent a valved anatomic site within the heart. In particular, the improved prosthetic heart valve delivery systems and methods of the present disclosure provide more flexibility in the valve replacement procedure, ensure accurate and precise placement of the prosthetic heart valve with reduced reliance on imaging, and provide additional attachment of the prosthetic valve, reducing the incidence of valve migration or misalignment.

Various embodiments now will be described more fully hereinafter. Such embodiments may, however, be embodied in many different forms and should not be construed as limited to the embodiments set forth herein; rather, these embodiments are provided so that this disclosure will be thorough and complete, and will fully convey its scope to those skilled in the art.

It is additionally an object of the present invention to provide a valve prosthesis delivery system which facilitates delivery of a valve prosthesis to the heart while minimizing trauma or damage to the vessels and tissues of a patient. The various embodiments described herein provide a means for both pushing and pulling the valve prosthesis delivery system through the tight turns presented by the heart chambers. It is noted that for the purposes of describing the disclosed systems and methods, the term "proximal" refers to a relative position closer to a control unit whereas the term "distal" refers to a relative position further away from a control unit.

FIG. 1 illustrates a forward perspective view of an aortic valve prosthesis 100 with self-expanding frame in accordance with the present invention. The aortic valve prosthesis 100 is interchangeable referred to hereinafter as a valve frame assembly 100. The prosthesis 100 is spring-biased to apply expansive radial forces in opposition to the native anatomy of a patient thus securing the prosthesis 100 in position when deployed. The prothesis 100 comprises a frame 101, which may comprise a plurality of crisscrossing metal laths 111 forming a lattice-like cylindrical structure, or stent, which circumscribes one or more interiorly-disposed leaflets 103.

In the shown embodiments, the prosthesis is in a radially-dilated (or expanded) configuration but is delivered in a radially-contracted (or compressed configuration).

The prothesis 100 comprises a plurality of protuberating stabilization prongs 102, barbs, or hooks. These prongs 102 jut laterally from the frame 101 and may be declined toward a bottom of the frame 101. The prongs 102 are adapted to engage with the native anatomy surrounding a deployed prothesis 100 and reduce embolization or migration of the prosthesis 100 post PAVI within a patient. The prosthesis may include as few as one or as many of as 100 prongs 102. The prongs 102 in typical embodiments decline from the top of the prosthesis 100, but may incline in some embodiments. In still further embodiments, prongs 102 positioned near the top of the prosthesis 100 incline or decline while prongs 102 positioned near the bottom of the prothesis 100 angle in a opposing direction.

When the prosthesis is correctly positioned in the native aortic valve, the prongs 102 may hook or barb the aortic commissures and/or cusps of the aortic valve. The aortic valve is typically composed of three leaflets with cusps at the inflow (ventricular) portion of the valve and commissures at the outflow portion. These commissures are the structure of the adjoining leaflets. It is common after PAVI for the seal which a prothesis formed within the annulus to leak at the commissures. The prongs 102 help pull the commissures together around the outer circumference of the prothesis 100, helping to seal the prothesis 100 in place and prevent leakage and regurgitant blood.

The prothesis 100 comprises a plurality of leaflets 103 coupled to the frame 101 and disposed within a hollow interior recess 107 formed by the frame 101. The leaflets 103 may be formed from a flexible or semi-rigid bioinert material, including polymeric materials. The leaflets 103 form a check valve which prevents regurgitation of blood back into the ventricle. In other embodiments, the leaflets 103 comprise a homograft from a cadaver or autograft. The leaflets 103 may be formed as a single integrated piece, or valvular structure.

FIGS. 2A-5 illustrates perspective views of a delivery system 200 with contracted valve frame assembly in accordance with the present invention, including a handle 201. The delivery device 200 is adapted to facilitate mounting of any aortic valve prosthesis 100 in any axial orientation (outflow of the valve positioned in the direction of either the distal or proximal side). The contracted (or crimped) prosthesis 100 is mounted at the distal end 239 of a delivery sheath 207 that can be between 60 cm and 150 cm long. A proximal side 238 of the delivery system 200, 300, 400, 500, comprises a user handle 201. The contracted prothesis 100 may be between 3 mm and 10 mm in diameter. The expanded prothesis 100 may be between 15 and 40 mm in diameter. The sheath diameter 207 may be between 3 and 10 mm in diameter.

The distal end 239 of the delivery device 200 comprises a frustoconical tip 254 behind which the crimped prothesis 100 is mounted. The prothesis 100 is mounted, or inserted onto the sheath 207, to rest within a recess 256 defined between the frustoconical tip 254 and a tapered hub 258 on the sheath 207. The tapered hub 258 may comprise a frustocone with a hollow interior passage. A plurality of apertures 212 (or bores) form on a surface (such as the top surface) of the sheath 207 within the recess 256.

One or more lasso elements 208 exit, and protrude from, the apertures 212. The lasso elements 208 are shown in a contracted configuration (or state) in FIG. 3, in an expanded configuration in FIG. 4A, and in a semi-expanded configuration in FIG. 4B.

Figure 5:
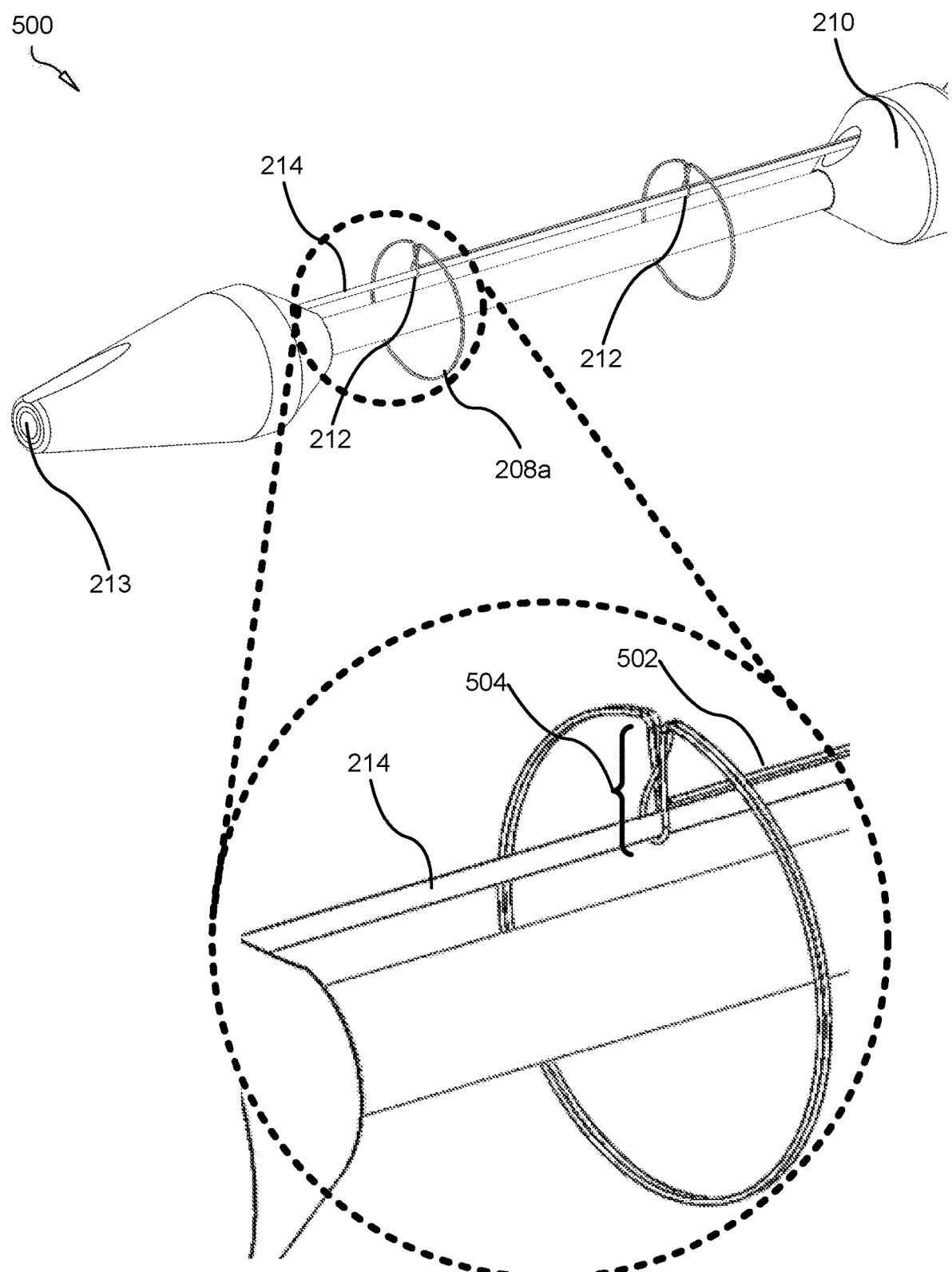
FIG. 5 illustrates a cutaway side perspective view of a distal end of a delivery system, with zoomed view thereof, in accordance with the present invention.

The lasso elements 208 protrude from the apertures 212 in the sheath 207 or lumen 211. FIG. 5 is a cutaway omitting the lumen 211 from view and showing an engagement pin 214 which traverses the lumen 211 longitudinally. The engagement pin 214 may be retracted using one or more of the controls 202 at the handle 201. The engagement pin 214 is interconnected to the handle 201 using a pull wire 502.

The pull wire 502 may be a separate flexible wire attached to the lasso elements 208 or integrated as a single piece therewith. The engagement pin 214 is inserted into one or more subloops 504 formed by the lasso elements 214 within the lumen 211.

Figure 4A:
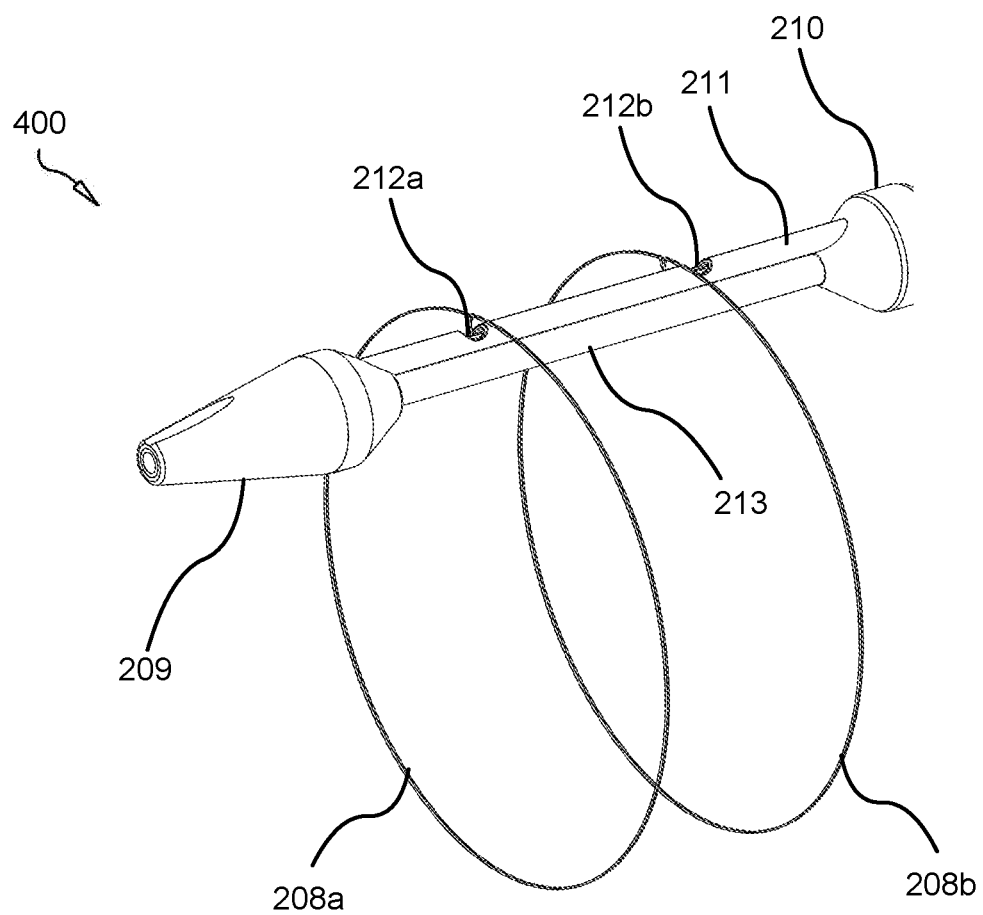
FIG. 4A illustrates a side perspective view of a distal end of a delivery system with a lasso in an extruded configuration in accordance with the present invention.
Figure 4B:
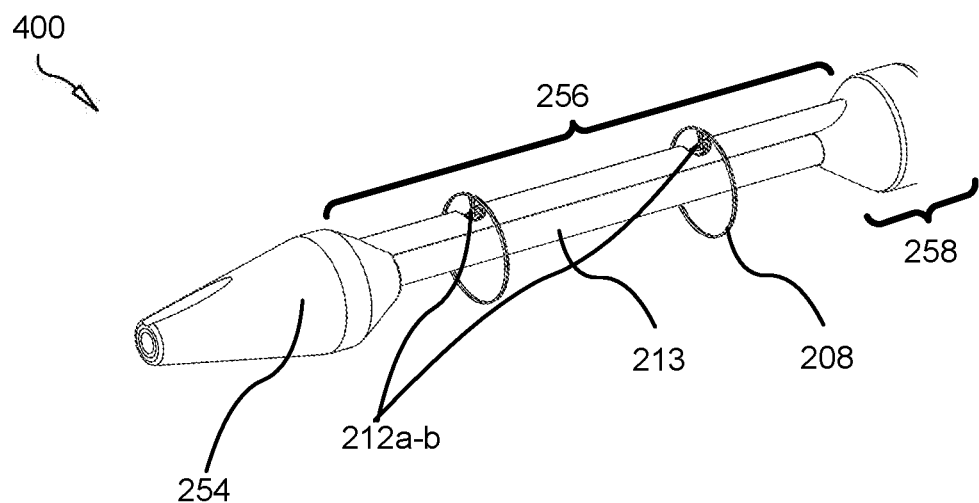
FIG. 4B illustrates a side perspective view of a distal end of a delivery system with a lasso in a semi-extruded configuration in accordance with the present invention.

Alternatively, the lasso elements 208 (and the pull wire 502) may traverse the hollow interior recess of the sheath 207 rather than a separate lumen. A nose cone shaft 213 that connects the nose cone to the user handle also provides a lumen for a guidewire 500 (further described below in relation to FIG. 6). FIG. 4b illustrates the state of the lasso 208 after an actuation of control 203 on the user handle 201 to reduce the diameter of lassos 208a-b.

The lasso elements 208 are adapted to circumscribe the prothesis 100 and crimp, or compress, the prothesis 100 when the control 203 is actuated. The lasso elements 208 pull the prothesis 100 inwardly radially into a contracted configuration. When the engagement pin 214 is retracted toward the proximal end of the delivery system 400, the lasso elements 208 are freed to expand, and thus allow the prothesis to expand, at the target location.

In various embodiments, the lasso elements 208 are formed from sutures, metallic braids, polyethylene, or other flexible materials known to those of skill in the art. The lasso elements 208 may be retracted after the prothesis 100 is deployed back into the sheath 207 in some embodiments. In other embodiments, the lasso elements 208 are cut at one end and the uncut end pulled out through the handle 201 after the prothesis 100 is deployed. In still further embodiments, the lasso elements 208 form part of the prothesis 100 itself, and are left in situ after the expanded prothesis 100 is deployed. Thus, the lasso elements 207 may form part of the prothesis 100 or the delivery system 200.

Figure 2A:
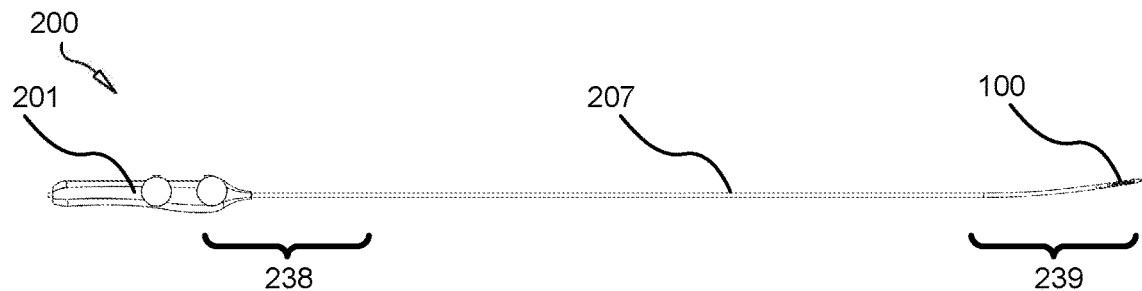
FIG. 2A illustrates a side perspective view of a delivery system with contracted valve frame assembly in accordance with the present invention.
Figure 2B:
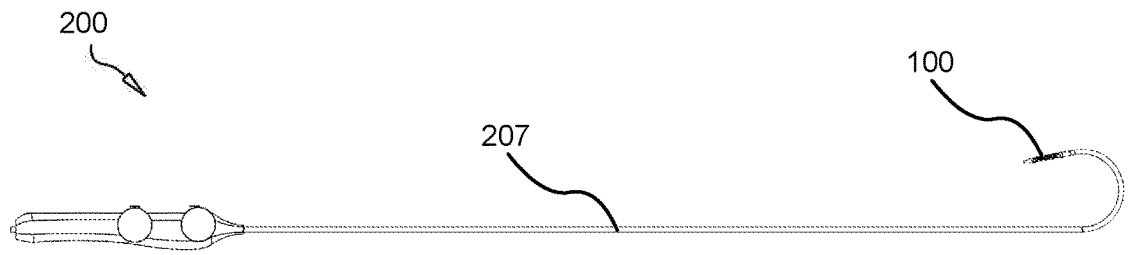
FIG. 2B illustrates a side perspective view of a delivery system with contracted valve frame assembly in accordance with the present invention.
Figure 2C:
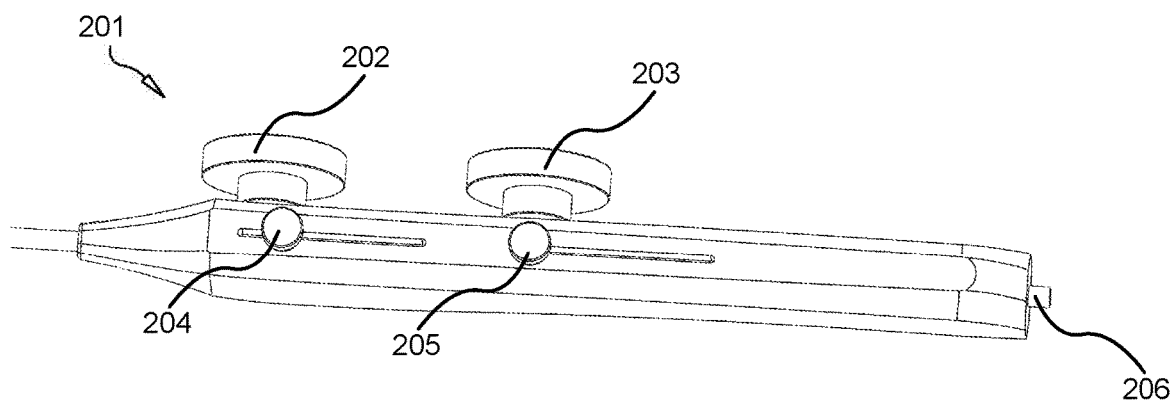
FIG. 2C illustrates a top perspective view of a delivery system in accordance with the present invention.
Figure 3:
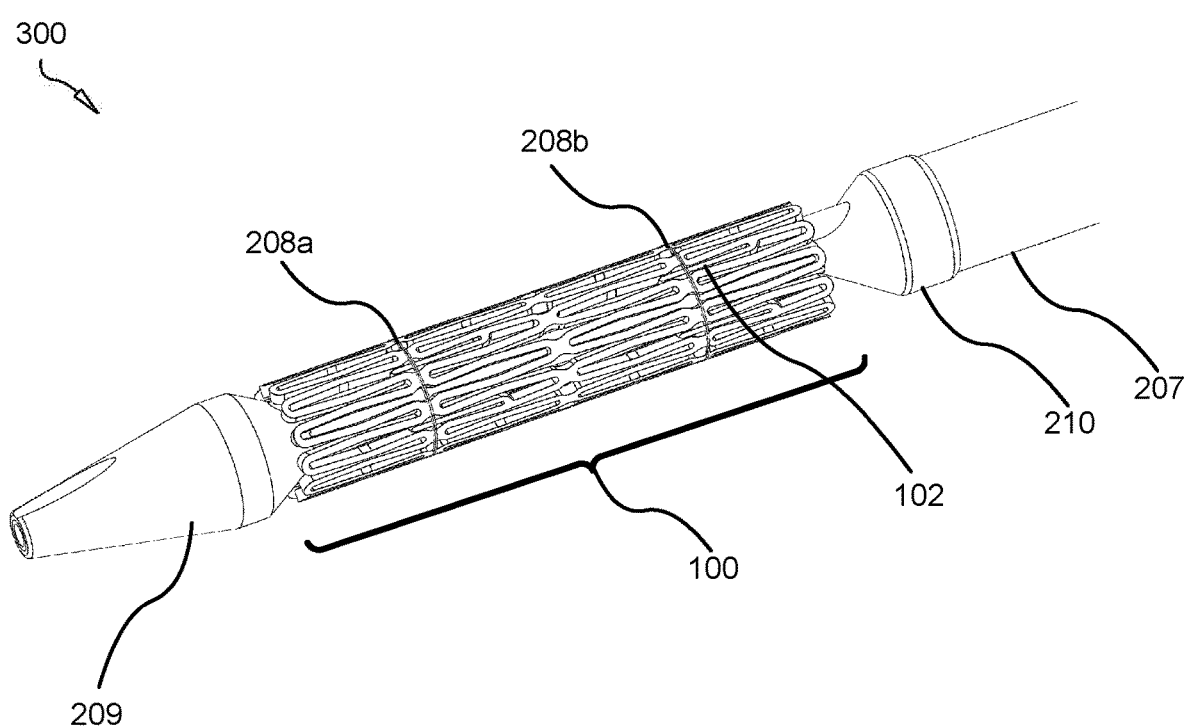
FIG. 3 illustrates a top perspective view of a valve frame assembly and delivery system in accordance with the present invention.

As illustrated in FIG. 2C a user handle 201 may consist of steering actuation control 202 and a surrounding lasso element control 203. The lasso element 208 may comprise suture, wire, monofilament, or other materials known to those of skill in the art. In some embodiments, friction or ratcheting elements may be incorporated into the handle 201 to further enhance operator control.

The controls 202-205 provide a selectively steerable delivery sheath 207 adapted to advance the crimped prothesis 100 through major vessels and/or arteries of the patient's circulatory system, including through the femoral artery and around one or more aortic arches.

The sheath 207 comprises a flexible, hollow, elongated tubular member forming an interior recess, or lumen, for housing one or more pull wires (or guidewires) traversing the sheath 207 longitudinally and affixed at proximal ends to the controls 202-205. Through the application of tensile force to the control wires using the controls 202-205, the curvature of the sheath 207 may be selectively manipulated during surgery and the prothesis 100 guided through the circulatory system to the target location within the patient's heart 602.

Control of the loop stabilization wire 215 (further described below) is realized via a sliding interface 204 to release or contract the annular loop 241 (or annular ring) formed by the loop stabilization wire 215. To disengage the prosthesis 100 from the delivery device 200, the sliding interface 205 is retracted to pull back the engagement pin 214 on the surrounding lasso element loop 208. The user handle 201 also defines a passage for common guidewires, and pull wires. The handle 201 includes a guide wire access point 206.

FIG. 2B illustrates a configuration of the delivery device 200 in a steered position after actuation of the steering control 202 which determines the degree and radius of flex of the distal portion 239 of the delivery device 200.

The delivery system 100 can be configured such that the heart valve prosthesis 100 is advanced through the vascular system while being movably coupled to the sheath 207, minimizing friction of the tip 209 and cross section of the delivery system 200, 300, 400, 500 with the tunica intima, tunica media and tunica adventitia of the blood vessels. The controls 202-205 and guidewires impart motion control and articulation to the sheath 207, providing a surgeon with control over the direction of travel of the contracted prosthesis 100 to the target location.

The sheath 207, in the shown embodiment, comprises a tip 209, which may be round or tapered. In those embodiments in which the tip 209 is frustoconical, the tip 209 is a frustoconical tip 254. In some embodiments, the delivery system 200 lacks a tip 209 altogether. In other embodiments, a cylindrical sleeve may telescope on the sheath 207 and be adapted to envelope the crimped prothesis 100 as it travels to the delivery point before the cylindrical sleeve is retracted telescopically using controls on the handle 201 to expose the crimped prothesis 100.

Figure 6:
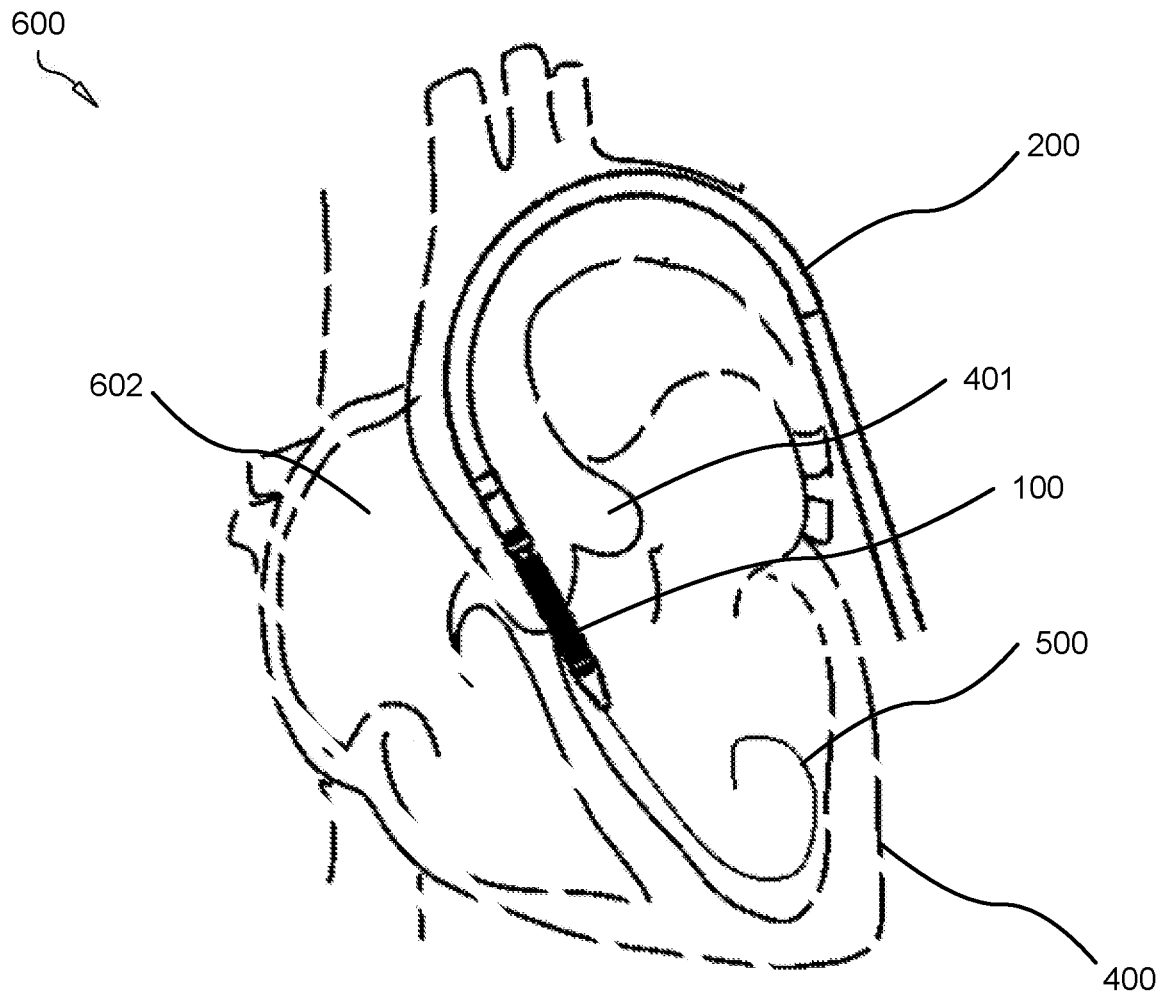
FIG. 6 illustrates an environmental side perspective view of a contracted valve frame assembly tracked to the aortic position using a delivery system in accordance with the present invention.

FIG. 6 illustrates an environmental side perspective view of a contracted valve frame assembly 600 tracked to the aortic position using a delivery system in accordance with the present invention. The native aortic valve may be diseased, stenotic and/or regurgitant.

Figure 7A:
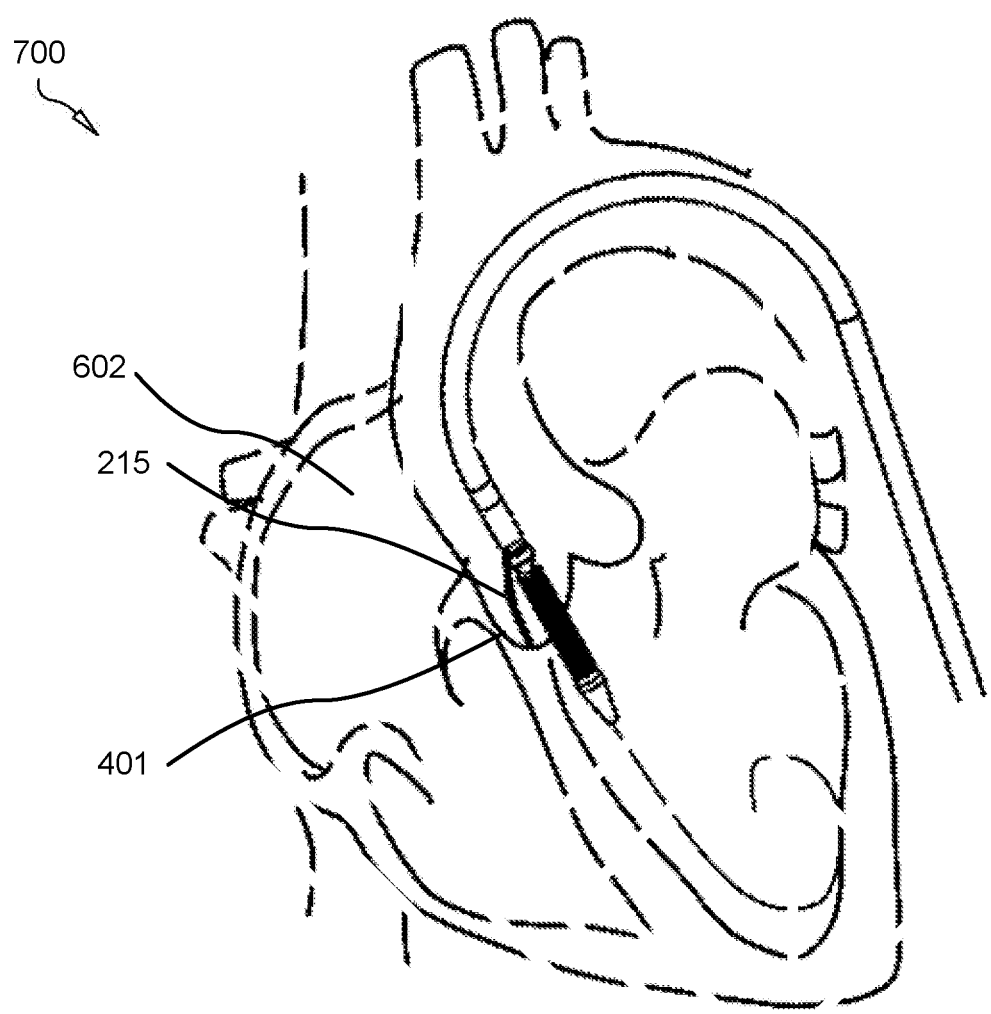
FIG. 7A illustrates an environmental side perspective view of a contracted valve frame assembly and delivery system with a stabilization loop deployed in at least one aortic sinus in accordance with the present invention.

FIG. 7A illustrates an environmental side perspective view of a contracted valve frame assembly and delivery system 700 with a stabilization loop 215 deployed in at least one aortic sinus of the heart 602 in accordance with the present invention. The stabilization loop 215 may be stabilized in at least one aortic sinus 401. The stabilization loop 215 is retractable to aid in aligning the prothesis 100 within the native valve anatomy.

Figure 7B:
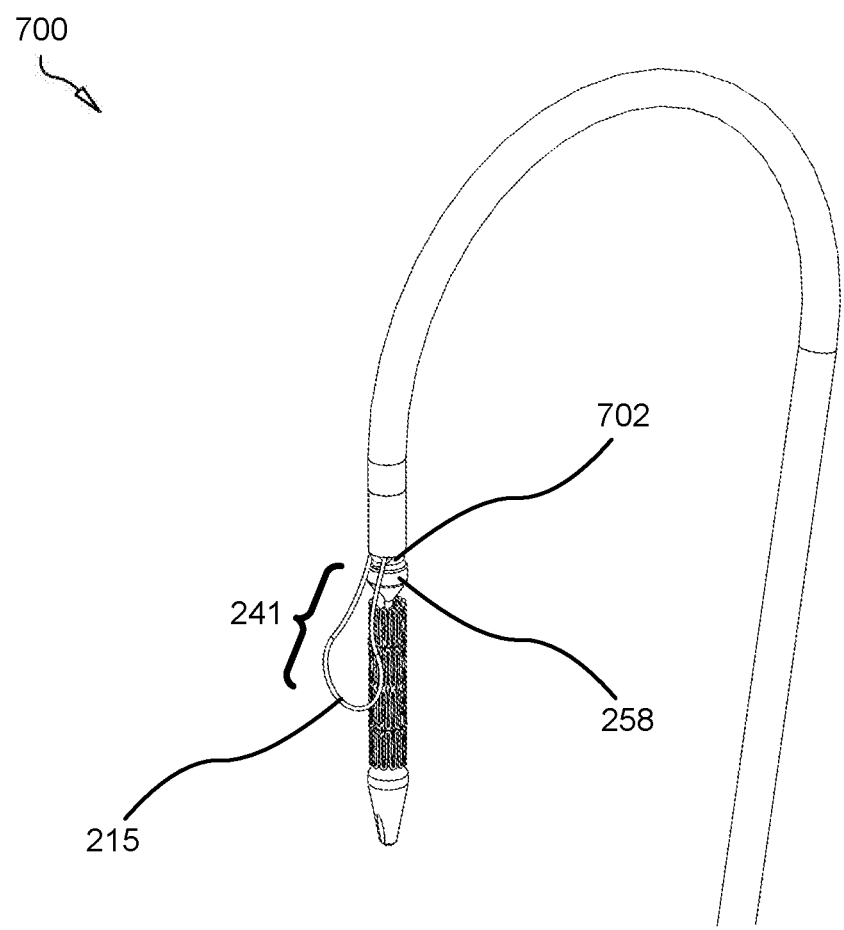
FIG. 7B illustrates a side perspective view of a contracted valve frame assembly and delivery system with a stabilization loop deployed in accordance with the present invention.

FIG. 7B illustrates a side perspective view of a contracted valve frame assembly and delivery system 700 with a stabilization loop 215 deployed in accordance with the present invention.

A second annular recess 702 may form behind the tapered hub 258, from which the stabilization loop 215 protrudes. The stabilization loop 215 juts at a declined angle from the sheath 207 and is adapted to engagement the soft tissue of the blood vessels. The stabilization loop 215 telescopes into and out of the sheath 207, applying both lateral and downward forces against the walls of the blood vessels and/or leaflets and/or ventricles of the heart 602. The stabilization loop 215 is connected to one or more controls 202-205 on the handle 201. The stabilization loop 215 is adjusted to position the prothesis 100 within the annulus 401 before final deployment of the prothesis 100 at the target area.

Figure 8:
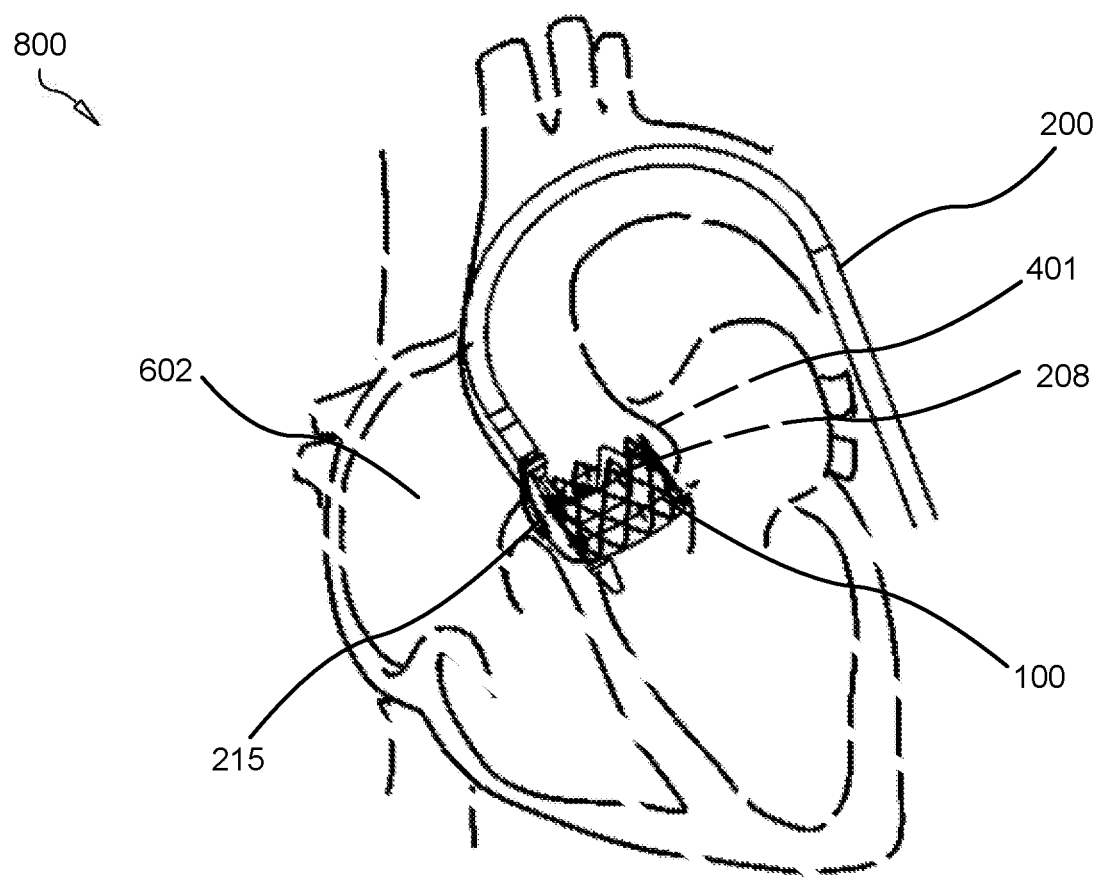
FIG. 8 illustrates an environmental side perspective view of a valve frame assembly and delivery system deployed at the native aortic valve in accordance with the present invention.

FIG. 8 illustrates an environmental side perspective view of a contracted valve frame assembly and delivery system deployed at the native aortic valve in accordance with the present invention. The lasso element 208 may be actuated to partially or completed reduce the valve diameter to remove or adjust the position of the prothesis 100.

Figure 9:
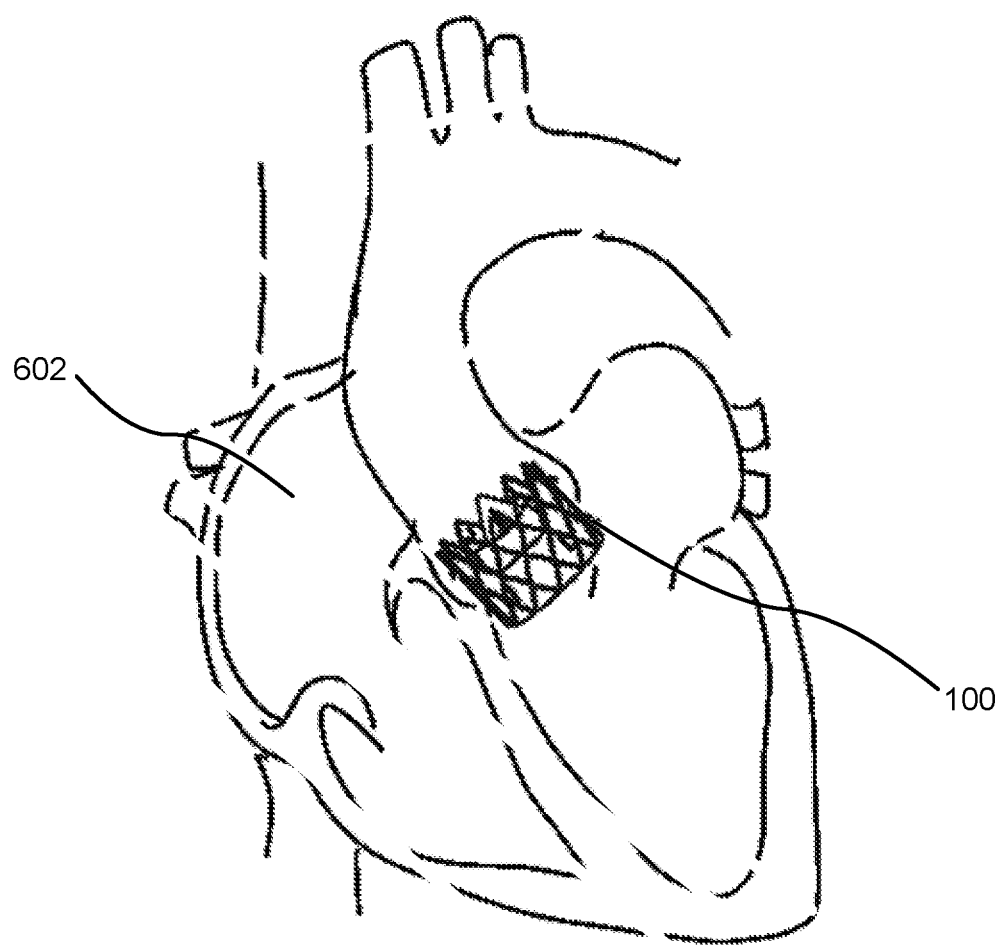
FIG. 9 illustrates an environmental perspective view of a deployed valve frame assembly in accordance with the present invention.

FIG. 9 illustrates an environmental perspective view of a deployed valve frame assembly in accordance with the present invention. Once the prothesis 100 is positioned and deployed, the deployment system 200 is removed leaving the prothesis 100 in place in the annulus 401.

Figure 10:
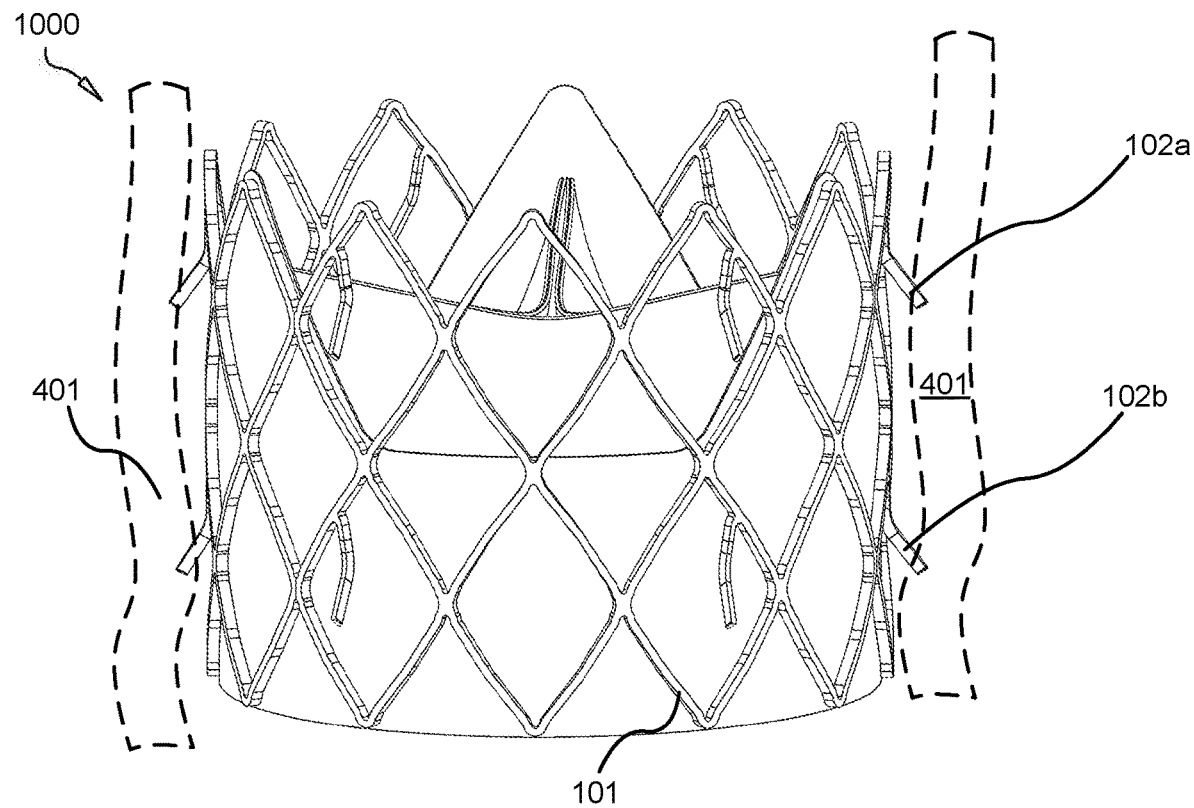
FIG. 10 illustrates a valve with stabilization prongs engaging native tissue in accordance with the present invention.

FIG. 10 illustrates a valve 100 with stabilization prongs 102 engaging native tissue of the annulus 401 in accordance with the present invention. The radial force of the metallic stent 101 and the prongs 102 anchor the prothesis 100 within the annulus 401.

Figure 11:
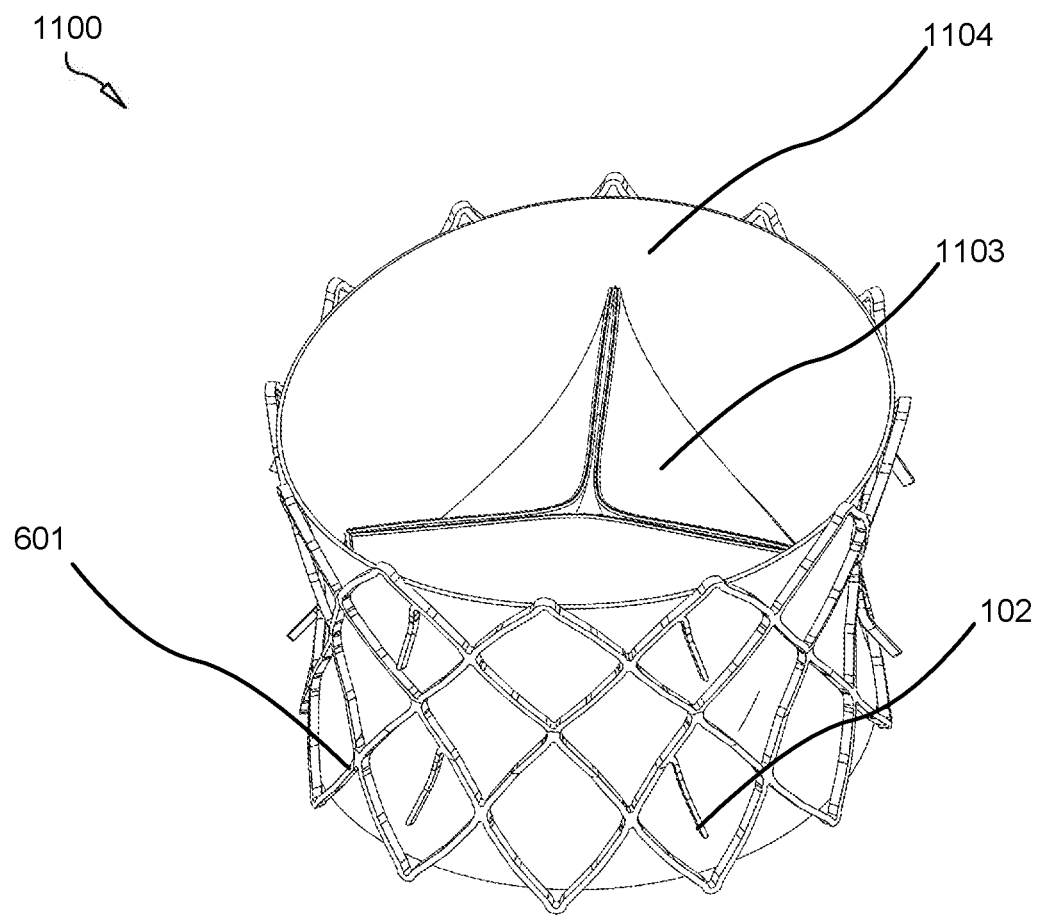
FIG. 11 illustrates a top forward perspective view of a mitral valve assembly in accordance with the present invention.

FIG. 11 illustrates a top forward perspective view of a mitral valve assembly 1100 in accordance with the present invention. The mitral valve assembly 1100 may have a waisted shape as shown (i.e., more narrow through the center between the top and bottom) to aid in axial location and anchoring in the native mitral valve position. The embodiment shown in FIG. 11 may be a mitral valve prothesis with a self-expanding frame which has sufficient radial expansion force to oppose the native anatomy and aid in securing its position. The frame 601 features a plurality of stabilization prongs 102 which further engage with the native anatomy to reduce embolization or migration of the valve prothesis. A plurality of flexible leaflets 1103 are attached to the frame 601 (or frame 102) via a membrane 1104. The membrane 1104 may be fabric, or made or organic, synthetic or polymeric materials. The membrane 1104 is also attached to the frame 601 and acts as a sealing surface against regurgitant blood flow.

Figure 12A:
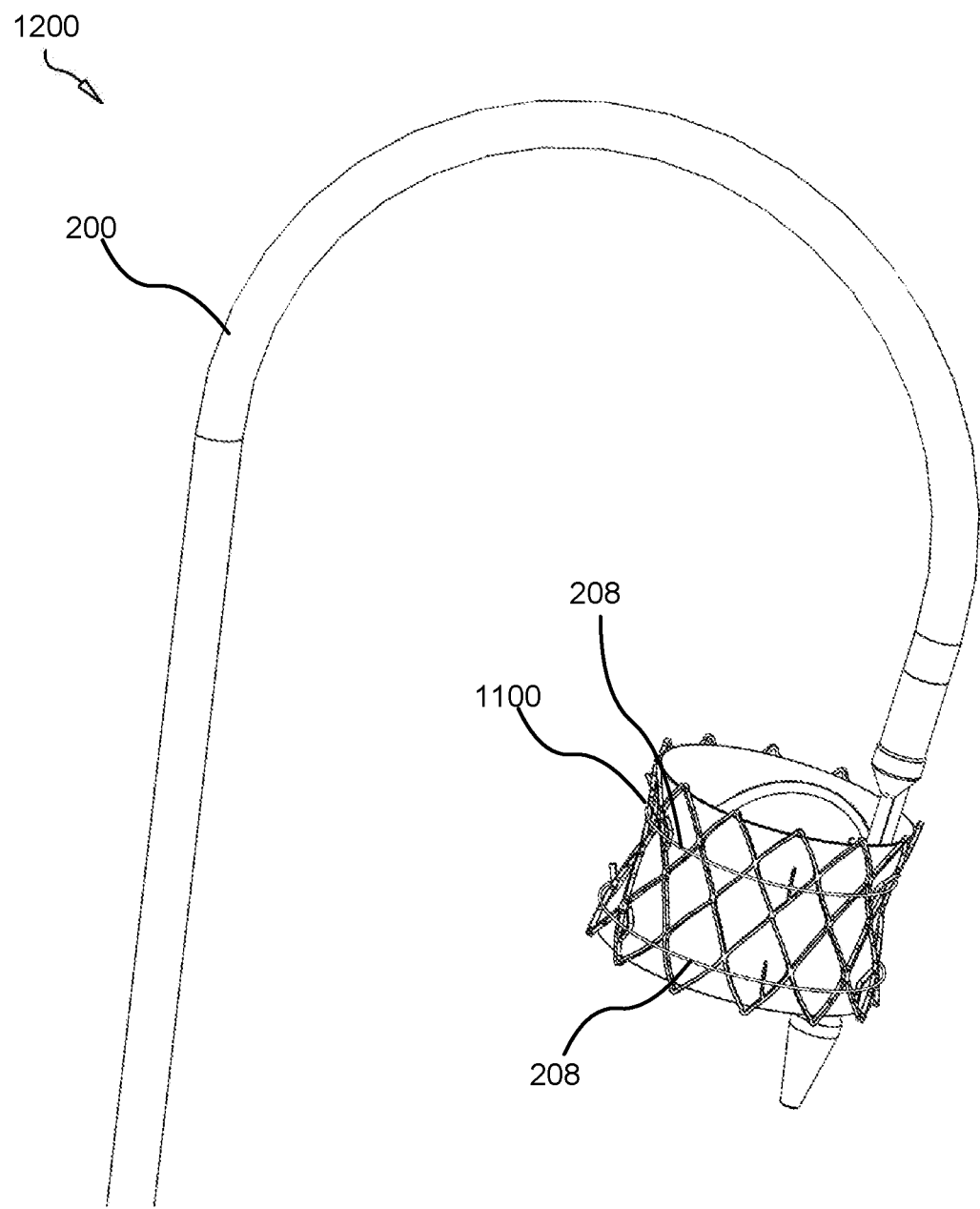
FIG. 12A illustrates a side perspective view of a mitral valve attached to a delivery system in accordance with the present invention.

FIG. 12A illustrates a side perspective view of a mitral valve 1100 attached to a delivery system 200 in accordance with the present invention. The valve 1100 is surrounded by lasso elements 208.

Figure 12B:
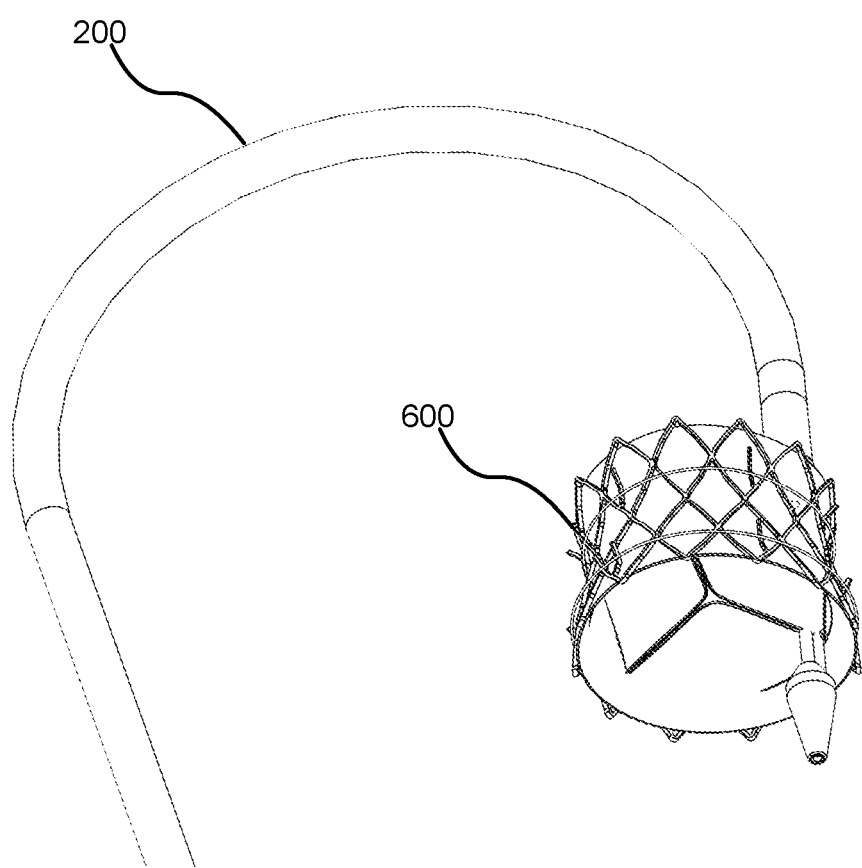
FIG. 12B illustrates a side perspective view of a mitral valve attached to a delivery system in accordance with the present invention.

FIG. 12B illustrates a side perspective view of a mitral valve 1100 attached to a delivery system 200 in accordance with the present invention. The outflow view of the valve 1100 is shown. This position represents the valve 1100 and delivery system 200 as it is routed through the inferior vena cava, transseptal atrial cross and crossing the mitral valve of the heart 602.

Figure 13:
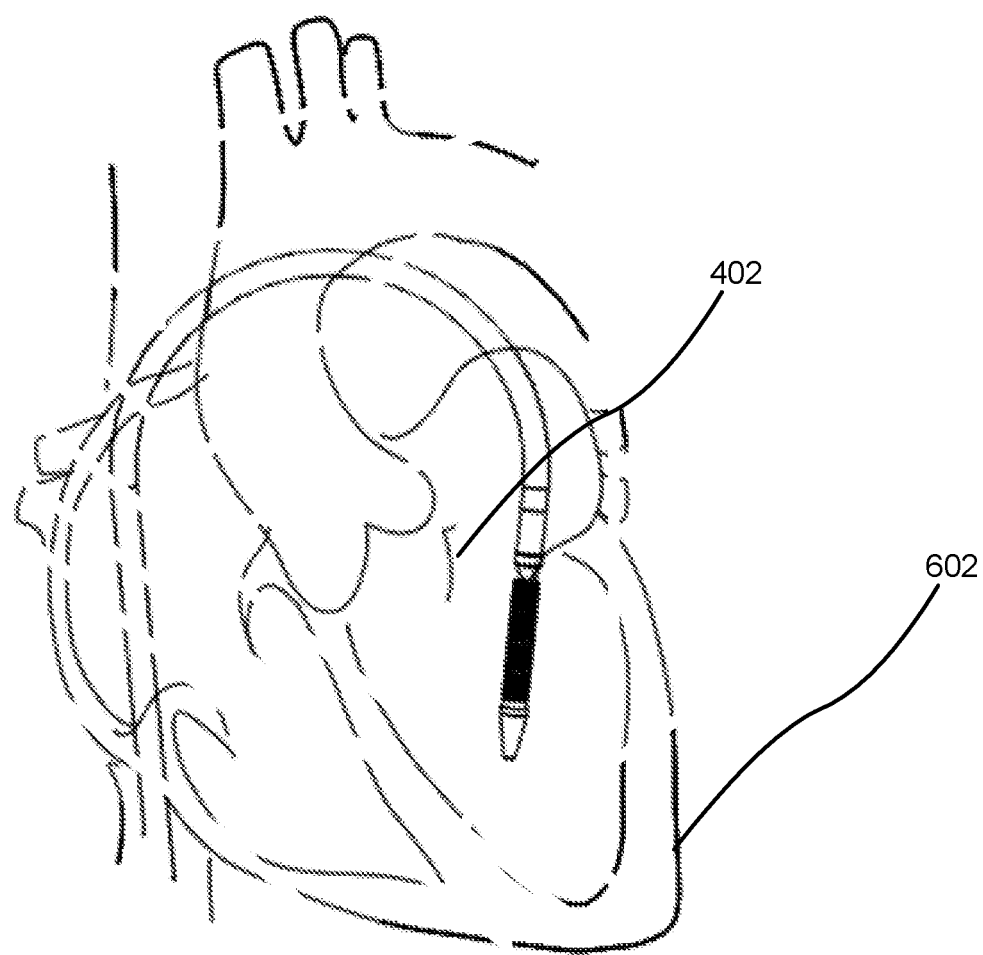
FIG. 13 illustrates a contracted mitral valve tracked to a general mitral valve position on a delivery system prior to deployment in accordance with the present invention.

FIG. 13 illustrates a cross section of the heart 602 showing the mitral valve 1100 tracked to a general mitral valve position using a delivery system 200 prior to deployment in accordance with the present invention.

Figure 14A:
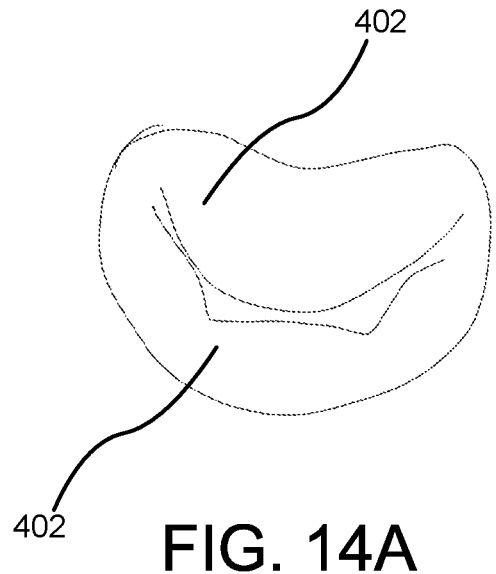
FIG. 14A illustrates the atrial side of the mitral valve.

FIG. 14A illustrates the atrial side of the mitral valve in accordance with the prior art. The anterior leaflet 403 and the posterior leaflet 404 are shown.

Figure 14B:
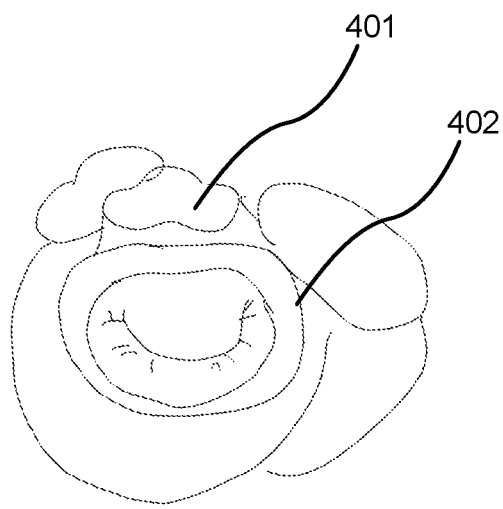
FIG. 14B illustrates a sectioned perspective view of the atrial side of the mitral valve.

FIG. 14B illustrates a sectioned perspective view of the atrial side of the mitral valve in accordance with the prior art.

Figure 14C:
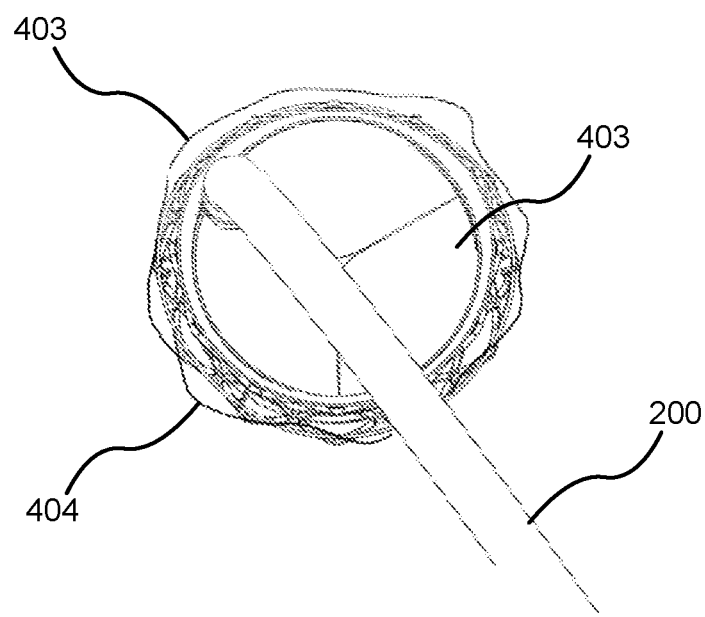
FIG. 14C illustrates an inflow view of the valve positioned into a mitral valve in accordance with the present invention.
Figure 15:
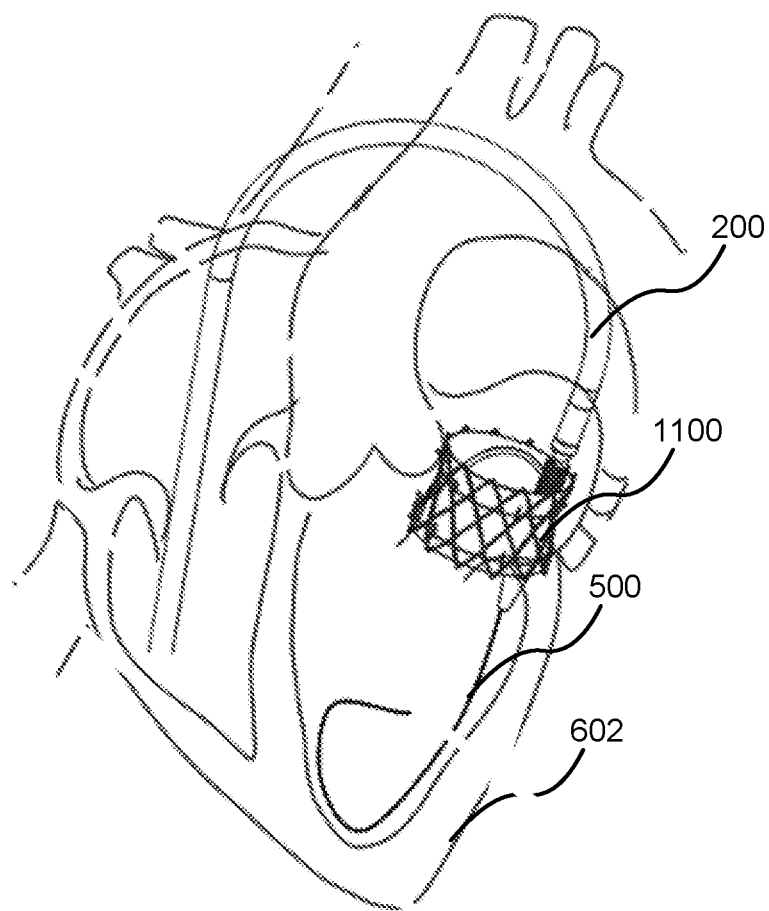
FIG. 15 illustrates an environmental perspective view of a deployed mitral valve still connected to the delivery device in accordance with the present invention.

FIG. 14C illustrates an inflow view of the valve positioned into a mitral valve in accordance with the present invention;

FIG. 15 illustrates an environmental perspective view of a deployed mitral valve still connected to the delivery device in accordance with the present invention. User control can be used to partially or completely retract the valve 1100.

Figure 16:
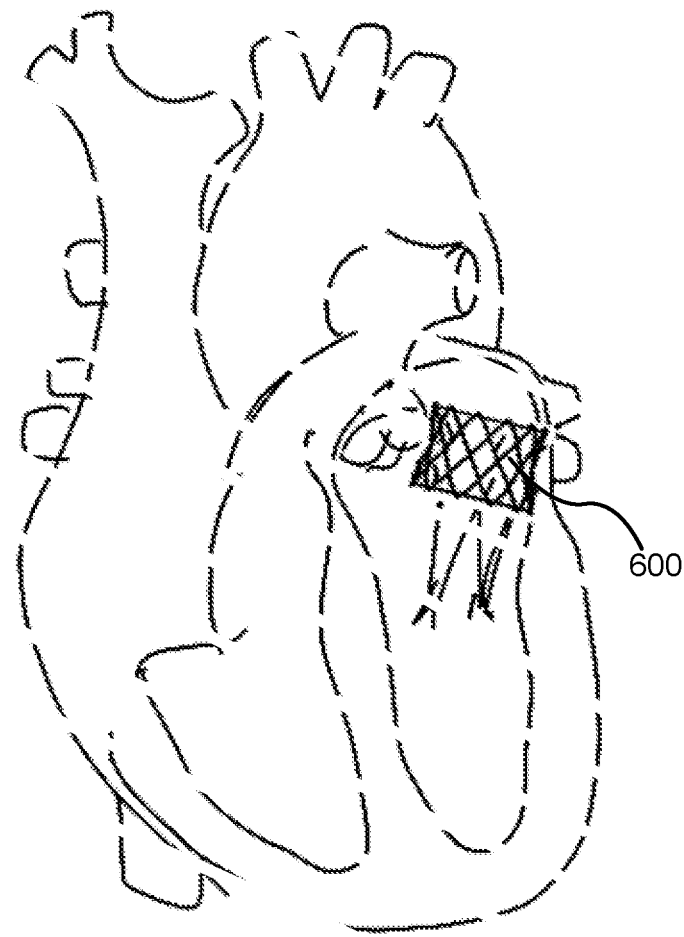
FIG. 16 illustrates an environmental perspective view of a deployed mitral valve with the delivery system withdrawn in accordance with the present invention.

FIG. 16 illustrates an environmental perspective view of a deployed mitral valve 1100 with the delivery system 200 withdrawn in accordance with the present invention.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A prosthetic heart valve and delivery system comprising:
   a spring-biased, metallic stent adapted to radially expand and contract comprising:
      a plurality of crisscrossing laths forming a cylindrical body, and
      a flexible check valve formed from one or more compressible valvular elements mounted within an interior recess formed by the crisscrossing laths;
      a plurality of declined stabilization prongs protruding laterally from one or more laths in the expanded metallic stent configuration;
   a selectively steerable delivery system comprising:
      a handle comprising a plurality of controls adapted to apply tensile force to one or more pull wires, the handle defining a hollow through passageway,
      an elongated sheath affixed at a proximal end to the handle, the elongated sheath comprising a flexible tubular member;
      wherein the elongated sheath is between 60 and 150 cm long on a longitudinal axis;
      wherein the one or more pull wires longitudinally traverse a lumen within the delivery system;
      one or more stabilization wire(s) forming annular rings at a distal end of the sheath, the annular rings adapted to receive, circumscribe and crimp the metallic stent, the stabilization wires protruding from one or more apertures on the distal end, the stabilization loops forming one or more subloops within one of the sheath and a lumen;
      an engagement pin detachably inserted into the subloop(s) of the stabilization wire(s), the engagement pin connected with a pull wire to a control on the handle, the engagement pin adapted to retract proximally out of the subloop(s) when the control is activated, the engagement pin adapted to release the annular rings and allow the metallic stent to expand;
      a frustoconical tip;
   wherein the sheath defines an annular recess at a distal end behind the frustoconical tip, the annular recess adapted to receive the metallic stent in compressed configuration.

2. The prosthetic heart valve and delivery system comprising of claim 1, wherein the lumen is the elongated sheath.

3. The prosthetic heart valve and delivery system comprising of claim 1, wherein the one or more loop stabilization wire(s) are positioned within the annular recess.

4. The prosthetic heart valve and delivery system comprising of claim 1, wherein the metallic stent is detachably circumscribed by the loop stabilization wires.

5. The prosthetic heart valve and delivery system comprising of claim 1, further comprising a tapered hub at the distal end behind the frustoconical tip.

6. The prosthetic heart valve and delivery system comprising of claim 1, wherein the frustoconical tip defines a hollow nose cone passageway traversing the frustoconical tip longitudinally.

7. The prosthetic heart valve and delivery system comprising of claim 1, wherein the one or more loop stabilization wire(s) form subloops within the annular recess.

8. The prosthetic heart valve and delivery system comprising of claim 1, wherein the compressed metallic stent is between 3 mm and 10 mm in diameter and the expanded metallic stent is between 10 mm and 40 mm in diameter.

9. A prosthetic heart valve and delivery system comprising:
   a spring-biased, metallic stent adapted to radially expand and contract comprising:
      a plurality of crisscrossing laths, and
      a flexible check valve formed from one or more compressible valvular elements mounted within an interior recess formed by the crisscrossing laths;
      a plurality of stabilization prongs protruding laterally from one or more laths in the expanded metallic stent configuration;
   a selectively steerable delivery system comprising:
      a handle comprising a plurality of controls adapted to apply tensile force to one or more pull wires, the handle defining a hollow through passageway,
      an elongated sheath affixed at a proximal end to the handle, the elongated sheath comprising a flexible tubular member;
      wherein the elongated sheath is between 60 and 150 cm long on a longitudinal axis;
      wherein the one or more pull wires longitudinally traverse a lumen within the delivery system;
      one or more stabilization wire(s) forming annular rings at a distal end of the sheath, the annular rings adapted to receive, circumscribe and crimp the metallic stent, the stabilization wires protruding from one or more apertures on the distal end, the stabilization loops forming one or more subloops within one of the sheath and a lumen;
      an engagement pin detachably inserted into the subloop(s) of the stabilization wire(s), the engagement pin connected with a pull wire to a control on the handle, the engagement pin adapted to retract proximally out of the subloop(s) when the control is activated, the engagement pin adapted to release the annular rings and allow the metallic stent to expand;

a tapered tip;

a tapered hub forming a second annular recess through which a rigid stabilization loop protrudes;

a rigid stabilization loop adapted to telescope relative to the frustoconical tip, the rigid stabilization loop declining laterally and toward the distal end, the rigid stabilization loop adapted to engage soft tissue and adjust positioning of the delivery system within a patient's circulatory system;

wherein the sheath defines an annular recess at a distal end behind the frustoconical tip, the annular recess adapted to receive the metallic stent in compressed configuration;

wherein the one or more loop stabilization wire(s) form subloops within the annular recess.

10. The prosthetic heart valve and delivery system comprising of claim 9, wherein the metallic stent is detachably circumscribed by the loop stabilization wires.

11. The prosthetic heart valve and delivery system comprising of claim 9, further comprising a tapered hub at the distal end behind the frustoconical tip.

12. The prosthetic heart valve and delivery system comprising of claim 9, wherein the frustoconical tip defines a hollow nose cone passageway traversing the frustoconical tip longitudinally.

* * * * *